(12) United States Patent
Safarevich et al.

(10) Patent No.: US 7,787,961 B1
(45) Date of Patent: Aug. 31, 2010

(54) REDUCED-DIAMETER BODY-IMPLANTABLE LEADS AND METHODS OF ASSEMBLY

(75) Inventors: Sergey Safarevich, Valencia, CA (US); Benedict L. Gomperz, North Hollywood, CA (US); Steve Norling, Canyon Country, CA (US); Serdar Unal, Los Angeles, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 480 days.

(21) Appl. No.: 11/776,239

(22) Filed: Jul. 11, 2007

(51) Int. Cl.
*A61N 1/05* (2006.01)
(52) U.S. Cl. ...................................... 607/116
(58) Field of Classification Search ............... 607/116, 607/119, 122
See application file for complete search history.

(56) References Cited

U.S. PATENT DOCUMENTS

| | | | |
|---|---|---|---|
| 5,014,720 A * | 5/1991 | Barcel et al. ............. | 607/122 |
| 5,488,768 A | 2/1996 | Mar | |
| 5,569,883 A * | 10/1996 | Walter et al. ............. | 174/84 R |
| 5,676,694 A | 10/1997 | Boser et al. | |
| 5,845,396 A * | 12/1998 | Altman et al. ............. | 29/885 |
| 6,018,683 A | 1/2000 | Verness et al. | |
| 6,026,567 A | 2/2000 | Swoyer et al. | |
| 6,061,595 A * | 5/2000 | Safarevich ............. | 607/37 |
| 6,119,042 A | 9/2000 | Verness et al. | |
| 6,285,910 B1 | 9/2001 | Verness et al. | |
| 6,456,888 B1 * | 9/2002 | Skinner et al. ............. | 607/116 |
| 6,501,993 B2 * | 12/2002 | Morgan et al. ............. | 607/122 |
| 6,697,675 B1 * | 2/2004 | Safarevich et al. ......... | 607/116 |
| 6,785,576 B2 | 8/2004 | Verness | |
| 2002/0099430 A1 | 7/2002 | Verness | |
| 2004/0015221 A1 * | 1/2004 | Kuzma ...................... | 607/116 |
| 2005/0113896 A1 * | 5/2005 | Pavlik et al. ................ | 607/122 |
| 2006/0041293 A1 | 2/2006 | Mehdizaheh et al. | |
| 2007/0168007 A1 * | 7/2007 | Kuzma et al. ............... | 607/116 |

FOREIGN PATENT DOCUMENTS

WO  WO99/06104  2/1999

* cited by examiner

*Primary Examiner*—Carl H Layno
*Assistant Examiner*—Jessica Sarcione

(57) ABSTRACT

A body-implantable lead suitable for use in conjunction with implantable cardiac devices and method for assembling a body-implantable lead suitable for use in conjunction with implantable cardiac devices. The body-implantable lead includes a lead body having at least one inner lumen and at least one elongated conductor cable residing within the inner lumen. An end portion of the conductor cable is joined by an aligned weld joint directly to an end portion of a lead component. Exemplary lead components include, but are not limited to, an electrode member, an elongated conductive connector pin of a proximal connector, a conductor extending from a proximal end of a distal tip of the lead, and a second elongated conductor cable residing within a second inner lumen of the lead body.

12 Claims, 15 Drawing Sheets

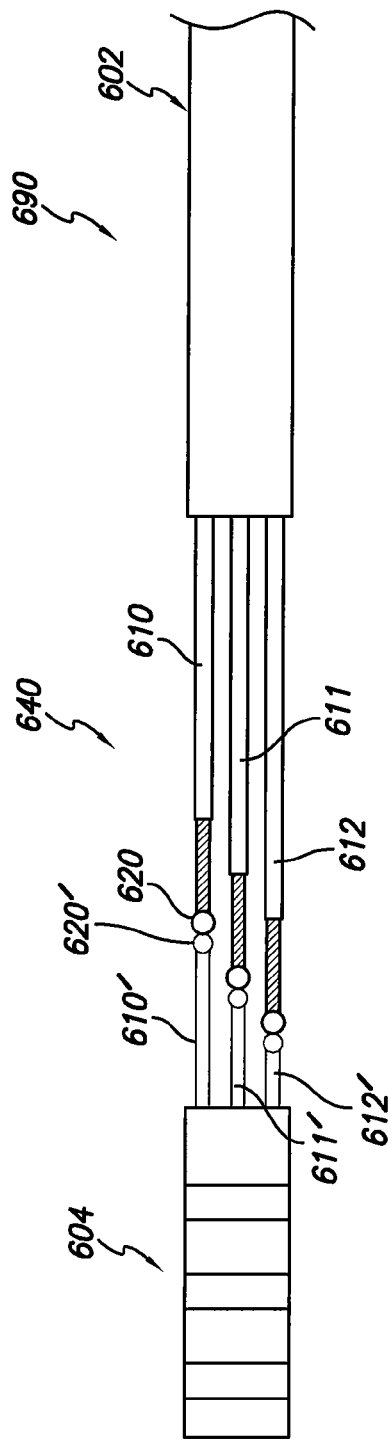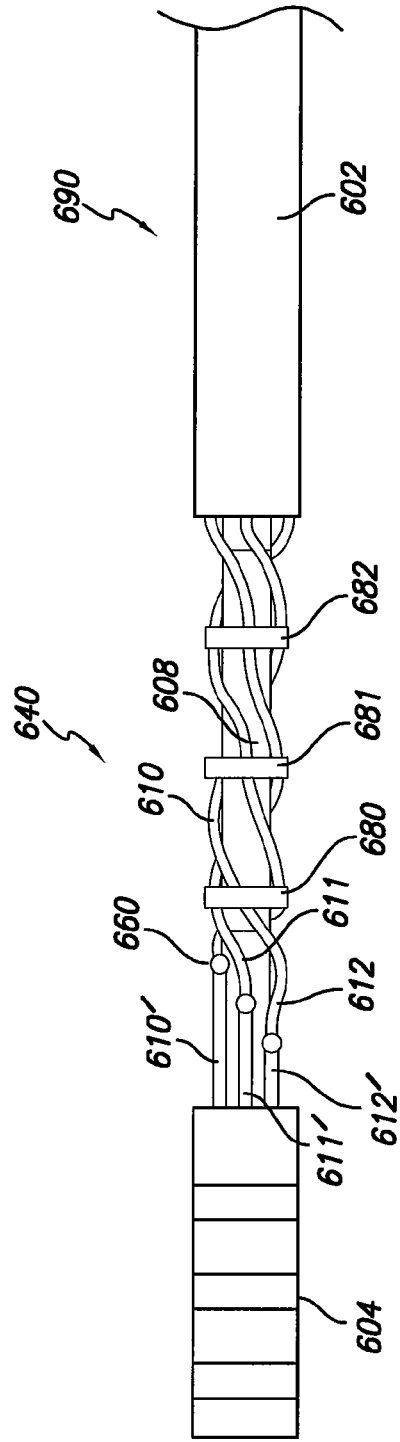

REDUCED-DIAMETER BODY-IMPLANTABLE LEADS AND METHODS OF ASSEMBLY

FIELD OF THE INVENTION

The present invention relates to body-implantable leads suitable for use in conjunction with implantable cardiac devices. More particularly, the present invention relates to reduced-diameter body-implantable leads and methods for their assembly.

BACKGROUND OF THE INVENTION

A body-implantable lead is used with an implantable cardiac device (ICD), such as an implantable pacemaker, a cardioverter, a defibrillator, a cardioverter defibrillator, and the like, to both sense cardiac function and deliver stimulation pulses to a desired tissue location. When the stimulating device is a cardiac pacemaker, for example, the lead, also referred to as a "pacing lead," connects the pacemaker's electrical circuitry directly with a desired chamber of the heart. One or more electrodes at or near a distal end of the lead placed inside of the heart contact the cardiac tissue at a desired location. The electrode(s) are electrically connected via insulated conductors within the lead to an appropriate connector at a proximal end of the lead. After an implantable lead is transvenously or otherwise implanted at the proper tissue location, the connector at the proximal end of the lead is detachably inserted into an appropriate mating connector of a medical device, such as a pacemaker, thereby electrically coupling the desired tissue location to the electrical circuits within the medical device. The distal tip of the implantable lead is held at a desired tissue location by either active fixation (such as a helix or hook) or passive fixation (such as a tine assembly near the distal electrode).

Body-implantable leads are generally designed to be pliant and flexible as to prevent damage to a patient's vasculature during implantation. Further, it is also desirable to minimize the overall diameter of the lead body, both to increase the pliancy and flexibility of the lead and to make the implantation of such leads as minimally invasive as possible, thus reducing operating room time and recovery time, and minimizing trauma at the introduction site and the likelihood of complications.

Despite the pliant and flexible nature of body-implantable leads, the repeated application of stress can fatigue individual conductors within the leads and eventually result in fracture. Therefore, lead bodies are typically reinforced in regions of expected high stress. For example, a reinforcing polyester cord or a reinforcing conducting coil may be disposed within the interior of a lead and extend the length of the lead. However, such reinforcements may substantially increase the diameter of the lead body and significantly reduce the flexibility of the lead.

The design of internal components for conductor joints of a body-implantable lead may also limit the minimum diameter of a lead body. For example, a conventional joint between an individual cable conductor and an electrode includes a transition member, such as a crimp sleeve, to join together the electrode and the conductor. FIG. 1A illustrates a conventional crimp joint 160 in which a cable conductor 102 is joined to a ring electrode 106 through a crimp sleeve 104. As shown, cable conductor 102 is joined to one end of crimp sleeve 104, and ring electrode 106 is joined to an opposite end of crimp sleeve 104. A conventional body-implantable lead may employ a number of such joints to connect individual conductors to connectors, electrodes, or additional conductors. As shown in FIG. 1B, each crimp joint may have an overall thickness of about 0.015 inches or more, and consequently, the use of transition members, such as crimp sleeves, crimp rings, and crimp slugs, within these conventional joints adds significant volume to the lead body, increasing its outer diameter $D_{OUT}$, decreasing its inner diameter $D_{IN}$, and reducing its flexibility. Further, the use of multiple transition members increases the manufacturing costs of the lead.

What is needed, therefore, is a more flexible, pliant body-implantable lead having improved conductor joints, thereby reducing the outer diameter of the lead in comparison to conventional devices.

SUMMARY

A body-implantable lead suitable for use in conjunction with implantable cardiac devices is presented herein. The body-implantable lead includes a lead body having at least one inner lumen and at least one elongated conductor cable residing within the inner lumen. An aligned weld joint directly joins an end portion of the conductor cable to an end portion of a lead component.

In one embodiment, the lead component is an elongated conductive connector pin of a proximal connector, and an aligned weld joint directly joins the end portion of the conductor cable to the end portion of the connector pin.

In another embodiment, the lead component is a conductor extending from a proximal end of a distal tip of the lead, and an aligned weld joint directly joins the end portion of the conductor cable to the end portion of the distal tip conductor.

In yet another embodiment, the lead component is an electrode member, and an aligned weld joint directly joins the end portion of the conductor cable to the end portion of the electrode member.

Methods for assembling a body-implantable lead suitable for use in conjunction with implantable cardiac devices are also presented herein. The method provides a lead body having at least one inner lumen with at least one elongate conductor cable residing within the inner lumen. The method joins an end portion of the conductor cable directly to an end portion of a lead component using an aligned weld joint.

In another embodiment, the lead component is an electrode member, and the method directly joins the end portion of the conductor cable to the end portion of the electrode member through an aligned weld.

In yet another embodiment, an iso-diametric lead body is formed by molding liquid insulation material about the conductor cable so as to substantially eliminate air gaps between the conductor cable and the lead body.

BRIEF DESCRIPTION OF THE DRAWINGS/FIGURES

The accompanying drawings, which are incorporated herein and form part of the specification, illustrate the apparatus and methods presented herein, and together with the description, the drawings further serve to explain the principles of and to enable a person skilled in the relevant art(s) to make and use the apparatus and methods presented herein. In the drawings, like reference numbers indicate identical or functionally similar elements.

FIGS. 6D-6F illustrate perspective views of steps of an exemplary method for constructing a second modular, body-implantable lead according to the embodiment of FIG. 6A.

DETAILED DESCRIPTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims. Thus, the operation and behavior of the present invention will be described with the understanding that modifications and variations of the embodiments are possible, given the level of detail presented herein.

In accordance with the embodiments presented herein, a flexible, pliant, body-implantable lead having crimp-less conductor joints is achieved using an aligned weld joint. An "aligned weld joint" as used herein refers to a joint having two or more conductors (such as a cable conductor or a wire) or a conductor and an electrode (such as a ring electrode) in which no additional transition members (such as crimp sleeves) are used and the conductor(s) is/are joined to the other conductor (s), or to the electrode as the case may be, so that the joint falls within an existing dimensional envelope as established by the conductors or as established by the electrode design. The existing dimensional envelope established by the conductors and electrode is determined by the dimensions of the conductors and the electrode prior to their connection through the aligned weld joint. Further description of exemplary aligned weld joints will be described with reference to FIGS. 2A-2E, 3A-3E, and 4A-4D.

Figure 1A:
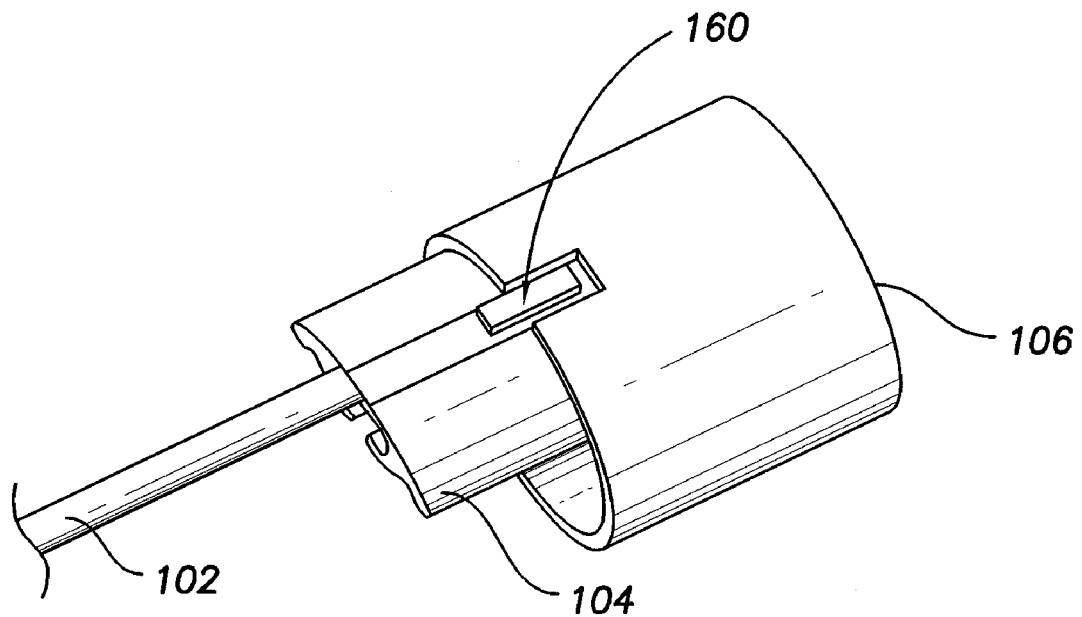
FIG. 1A illustrates a conventional joint between a cable conductor and a ring electrode.
Figure 1B:
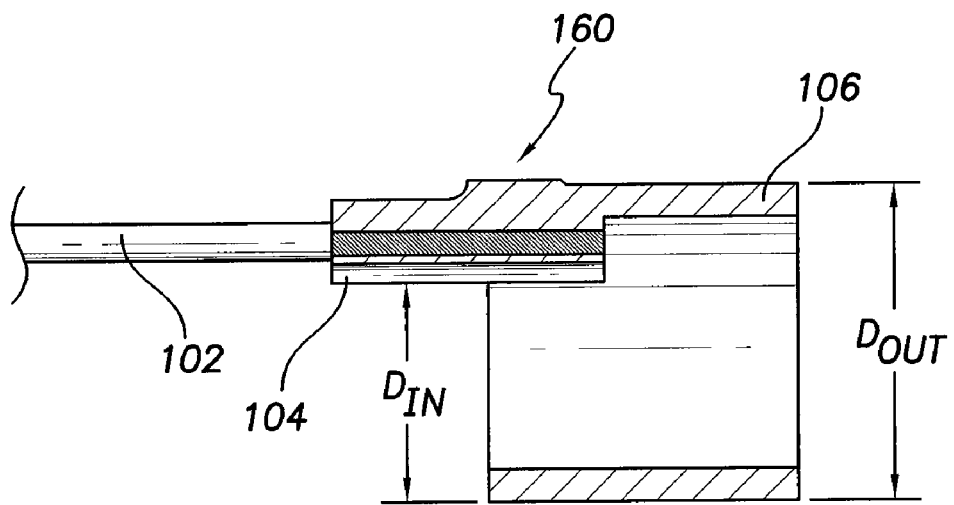
FIG. 1B is a cross-sectional view of the conventional joint shown in FIG. 1A.
Figure 2A:
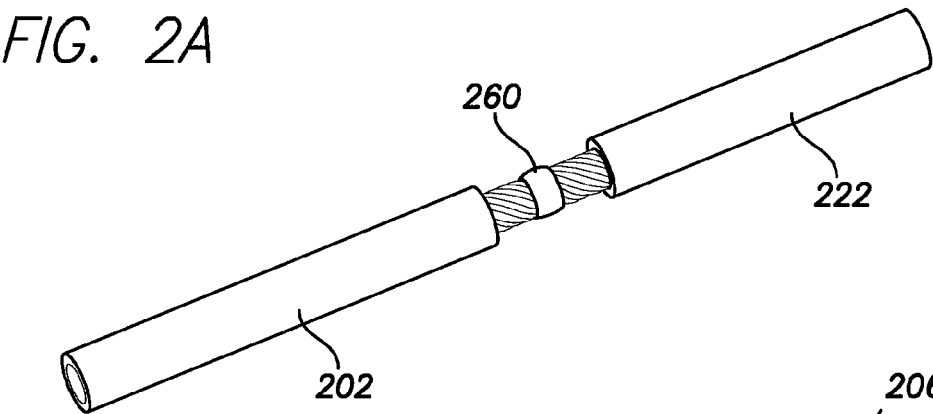
FIG. 2A illustrates an exemplary aligned weld joint that electrically and mechanically connects two coated cable conductors, in accordance with an embodiment presented herein.

FIG. 2A is a perspective view of an exemplary aligned weld joint 260 that forms an electrical and mechanical connection between a first coated cable conductor 202 and a second coated cable conductor 222. Unlike the conventional weld joint described in FIGS. 1A and 1B, aligned weld joint 260 requires no additional hardware, such as crimp sleeves and transition members, or material, such as solder or flux, to connect first and second coated cable conductors 202 and 222. In further contrast to conventional weld joints, aligned weld joint 260 falls within an outer diameter of first and second coated cable conductors 202 and 222, and as such, aligned weld joint 260 falls within an existing dimensional envelope established by first and second coated cable conductors 202 and 222.

Figure 2B:
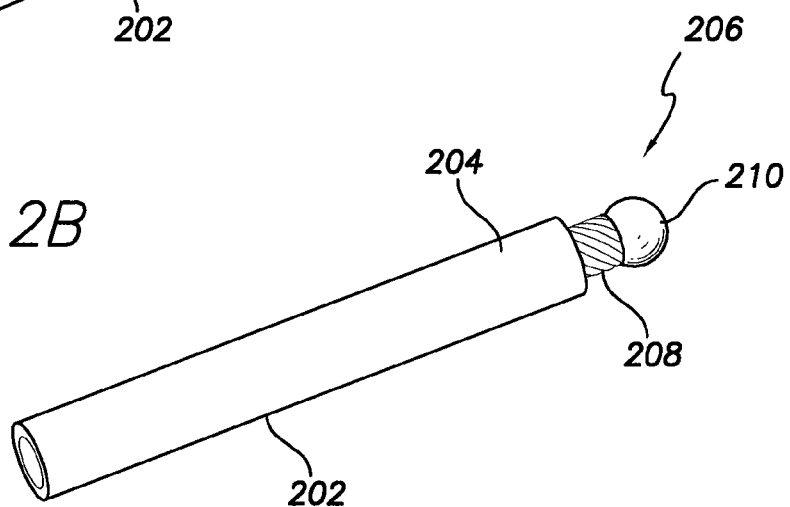
FIGS. 2B and 2C illustrate steps of an exemplary method for constructing an aligned weld joint in accordance with the embodiment of FIG. 2A.
Figure 2C:
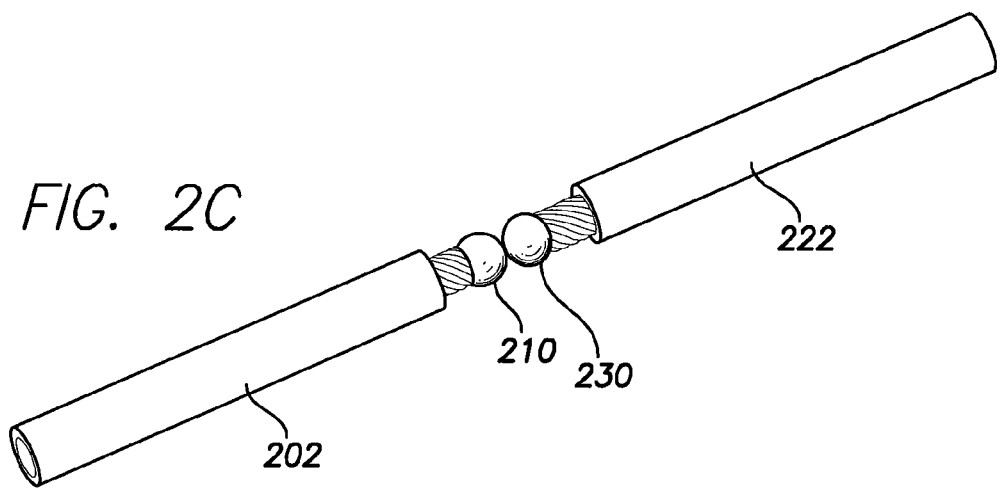

FIGS. 2B and 2C illustrate steps of an exemplary method for constructing aligned weld joint 260 shown in FIG. 2A. In FIG. 2B, laser energy has been applied to an end region 206 of first coated cable conductor 202 to ablate an insulative coating material 204 surrounding an underlying cable 208 and to melt underlying cable 208 to form a nugget 210. Nugget 210 is roughly spherical in shape, and the spherical shape of nugget 210 is a function of the material properties of underlying cable 208. Similarly, laser energy may also be applied to an end region of second coated cable conductor 222 shown in FIG. 2C to ablate its coating material and melt the underlying cable to form a nugget. Cable 208, or any other conductor (e.g., a solid wire) or electrode, may be formed of any conductive material, such as MP35N alloy, as is well known to those skilled in the art.

In FIG. 2C, first coated cable conductor 202 is aligned in a coaxial fashion with second cable conductor 222 such that nugget 210 of first cable conductor 202 is in contact with a nugget 230 of second cable conductor 222. Laser energy is then applied to fuse nuggets 210 and 230 into aligned weld joint 260, thereby establishing an electrical and mechanical connection between first cable conductor 202 and second cable conductor 222, as shown in FIG. 2A. The aligned weld joint requires no additional hardware or material to connect first and second coated cable conductors 202 and 222, respectively, and resulting joint 260 falls within the existing dimensional envelope established by first and second coated cable conductors 202 and 222.

Figure 8A:
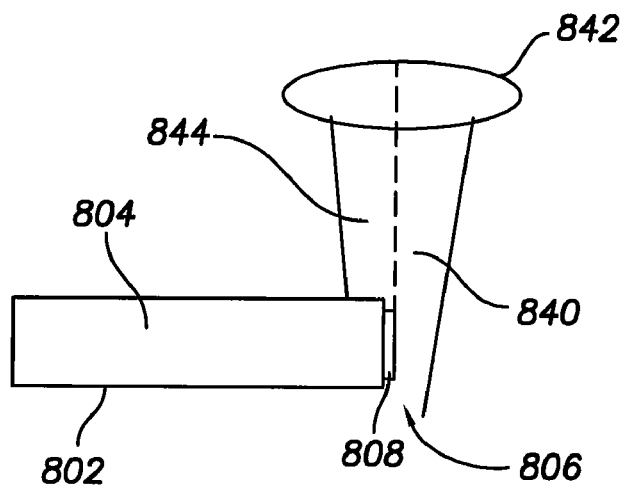
FIGS. 8A and 8B are examples that further describe the exemplary method for constructing an aligned weld joint according to the embodiment of FIGS. 2B and 2C.
Figure 8B:
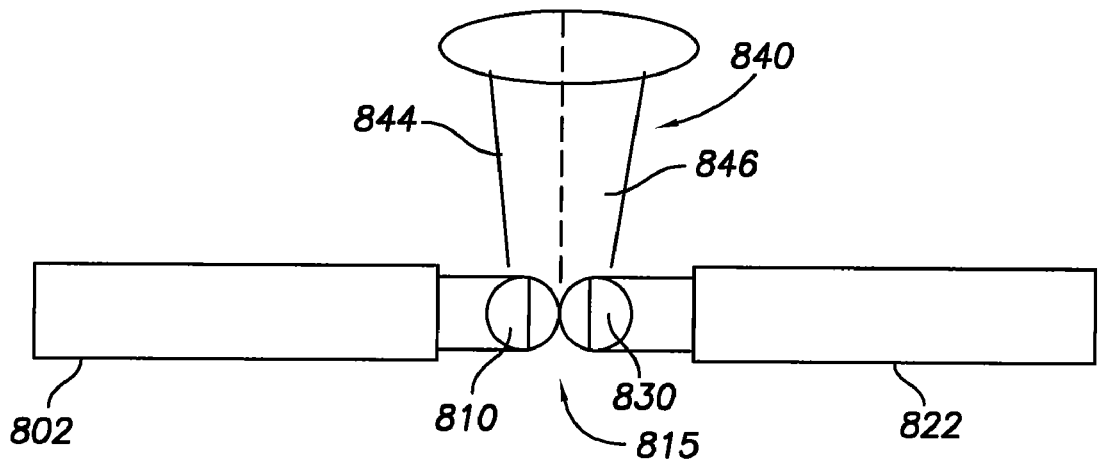

FIGS. 8A and 8B are examples further describing the exemplary method outlined in FIGS. 2B and 2C. In FIG. 8A, laser energy is focused through an optical element 842 to form a focused laser beam 840, and a first half 844 of focused laser beam 840 is delivered to an end region 806 of a first coated cable conductor 802. First half 844 of focused laser beam 840 ablates an insulative coating material 804 surrounding an underlying cable 808 and melts underlying cable 808 to form a nugget 810 (shown in FIG. 8B), similar to as nugget 210 in FIG. 2B.

In FIG. 8B, first coated cable conductor 802 is aligned in a coaxial fashion with a second cable conductor 822 such that nugget 810 of first cable conductor 802 is in contact with a nugget 830 of second cable conductor 822 in a contact region 815. Focused laser beam 840 is then delivered to contact region 815 to fuse nuggets 810 and 830 into an aligned weld joint, such as aligned weld joint 260 in FIG. 2C. In the example of FIG. 8B, first half 844 of focused laser beam 840 impacts nugget 810 and a second half 846 of focused laser beam 840 impacts nugget 830.

In the examples of FIGS. 8A and 8B, an intensity and a duration of focused laser beam 840 is constant, and as such, the same focused laser beam forms nuggets 810 and 830 and fuses nuggets 810 and 830 to form the aligned weld joint. Particular values of the intensity and the duration of focused laser beam 840 are material specific and depend upon a specific choice of cable conductors 802 and 822. For example, focused laser beam 840 could represent a 3.0 millisecond (ms) burst of 1.0 joules (J) of laser energy, although a number of acceptable combinations of intensity and duration would be apparent to one skilled in the art.

Figure 2D:
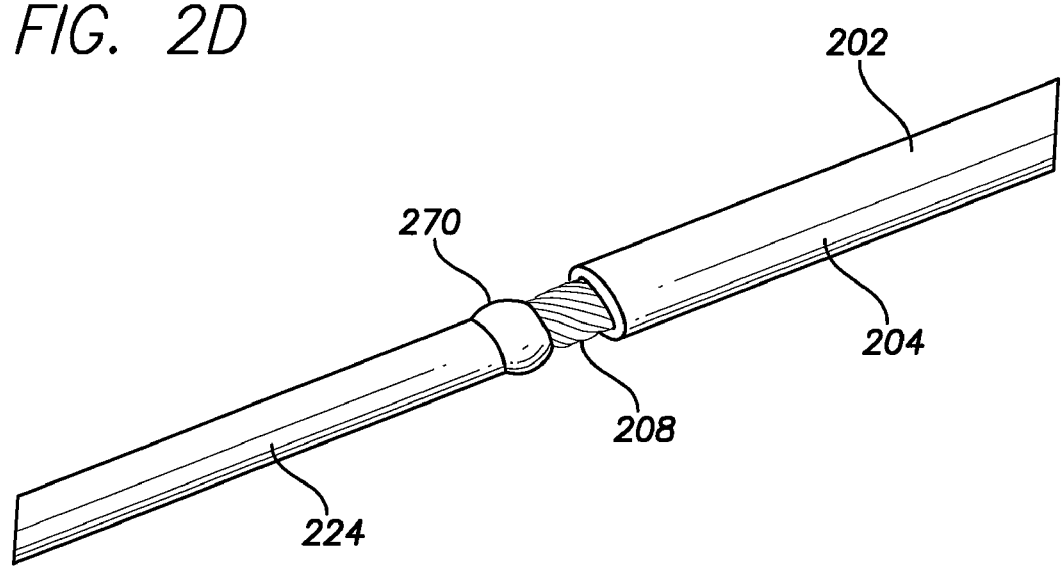
FIG. 2D illustrates an exemplary aligned weld joint that electrically and mechanically connects a coated cable conductor and an uncoated solid wire, in accordance with an embodiment presented herein.

The aligned weld joints described herein may also be used to join together a cable conductor and an uncoated solid wire conductor, such as a connector pin, or to join together two wire conductors. For example, FIG. 2D illustrates an exemplary aligned weld joint 270 that establishes a mechanical and electrical connection between coated cable conductor 202 and an uncoated solid wire 224. As was described above with reference to FIGS. 2A-2C, aligned weld joint 270 requires no additional hardware or material to connect coated cable conductor 202 with uncoated solid wire 224. Further, aligned weld joint 270 falls within an existing dimensional envelope established by cable 202 and solid wire 224.

Figure 2E:
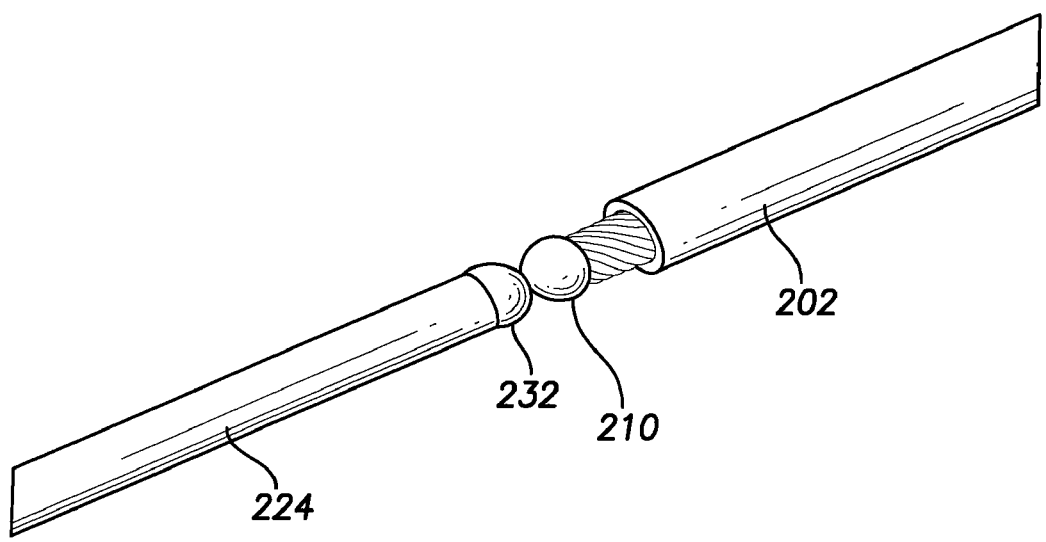
FIG. 2E illustrates a step of an exemplary method for constructing an aligned weld joint in accordance with the embodiment of FIG. 2D.

FIG. 2E illustrates a step of an exemplary method for constructing aligned weld joint 270 outlined above in FIG. 2D. In FIG. 2E, laser energy has been applied to coated cable conductor 202 to ablate coating material 204 and melt underlying cable 208 into nugget 210. In a similar fashion, laser energy has been applied to uncoated solid wire 224 to melt the wire material and form nugget 232. As shown, coated cable conductor 202 is then aligned coaxially with solid wire 222 such that nugget 210 of coated cable conductor 202 is in contact with nugget 232 of solid wire 224. Laser energy is then applied to fuse nuggets 210 and 232 into aligned weld joint 270, as shown in FIG. 2D, thereby establishing a mechanical and electrical connection between cable conductor 202 and uncoated solid wire 224.

As noted above, the aligned weld joints described herein may also join together a first uncoated solid wire and a second uncoated solid wire. In such an embodiment (not shown), a method similar to that described above may be used. For example, laser energy may be applied to an end of both the first and the second uncoated solid wires to melt the underlying wire material and form a nugget on each solid wire. The first and second solid wires are then aligned coaxially such that a nugget on the first solid wire would be in contact with a nugget on the second solid wire. Additional laser energy is then applied to fuse the nuggets into an aligned weld joint that electrically and mechanically connects the first and second solid wires. The aligned weld joint would require no additional hardware or material to connect the uncoated solid wires, and the joint falls within an existing dimensional envelope established by the solid wires.

Figure 3A:
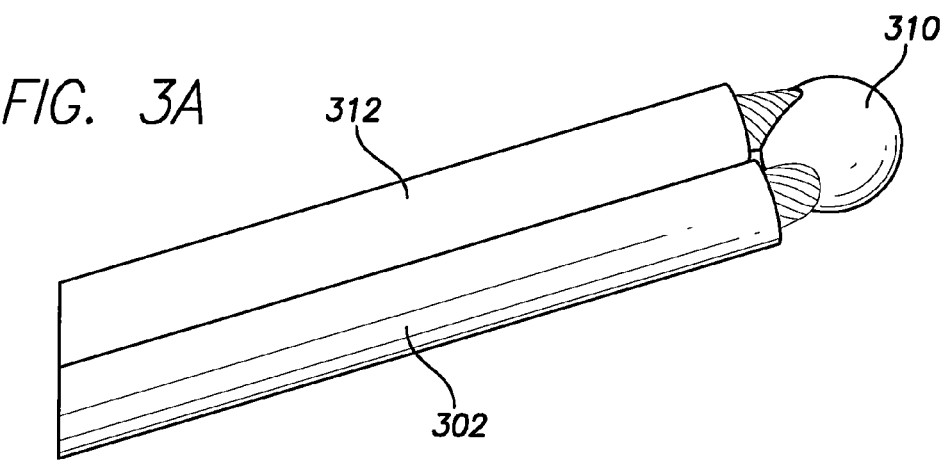
FIG. 3A illustrates an exemplary electrical and mechanical connection that joins together two coated cable conductors positioned along parallel axes, in accordance with an embodiment presented herein.

The aligned weld joints described herein join together conductors, such coated cable conductors and uncoated wires, that have been aligned in a coaxial fashion. In certain applications, it may be advantageous to weld end regions of two (or more) conductors together to form a common nugget and then connect these conductors with another one or more conductors using an aligned weld joint. Such applications may leverage the redundancy in electrical path provided by connecting multiple, side-by-side cables through an aligned weld joint. FIG. 3A illustrates an exemplary electrical and mechanical connection, or common nugget, 310 between two coated cable conductors 302 and 312 that are positioned side-by-side along parallel axes. In the embodiment of FIG. 3A, laser energy has been applied to an end region of each conductor to melt its underlying cable and form a nugget on each respective coated cable conductor. Coated cable conductors 302 and 312 are then aligned side-by-side along parallel axes such that the nuggets from each respective cable conductor are in contact, and laser energy is applied to fuse the individual nuggets into common nugget 310 that joins together cable conductors 302 and 312. Common nugget 310 thereby connects cable conductors 302 and 312 without the need for additional hardware or materials.

Figure 3B:
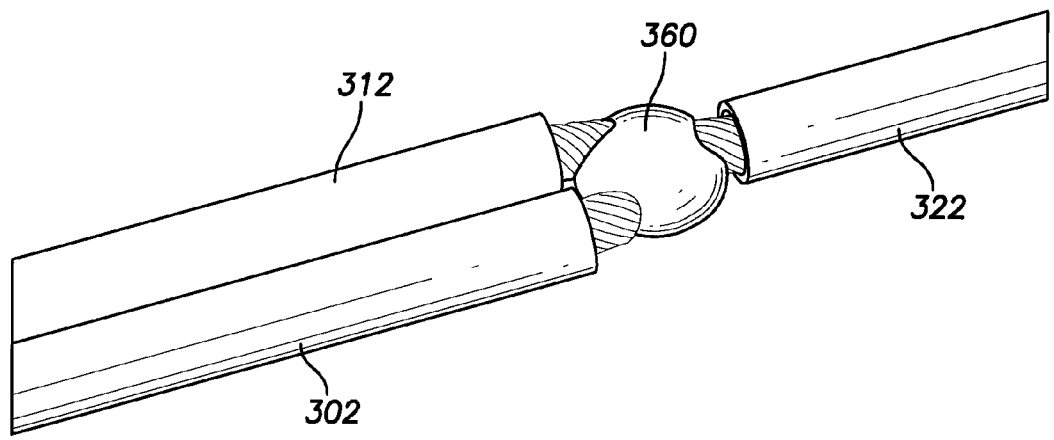
FIG. 3B illustrates an exemplary aligned weld joint that electrically and mechanically connects three coated cable conductors, in accordance with an embodiment presented herein.

FIG. 3B illustrates an exemplary aligned weld joint 360 that connects a third coated cable conductor 322 to the pair of coated cable conductors 302 and 312 that are joined together at their end regions by common nugget 310. Aligned weld joint 360 establishes an electrical and mechanical connection between third coated cable conductor 322 and each of the pair of coated cable conductors 302 and 312. Aligned weld joint 360 requires no additional hardware or material to join third cable conductor 322 to the pair of cable conductors 302 and 312, and aligned weld joint 360 falls within a dimensional envelope established by coated cable conductors 302, 312, and 322.

Figure 3C:
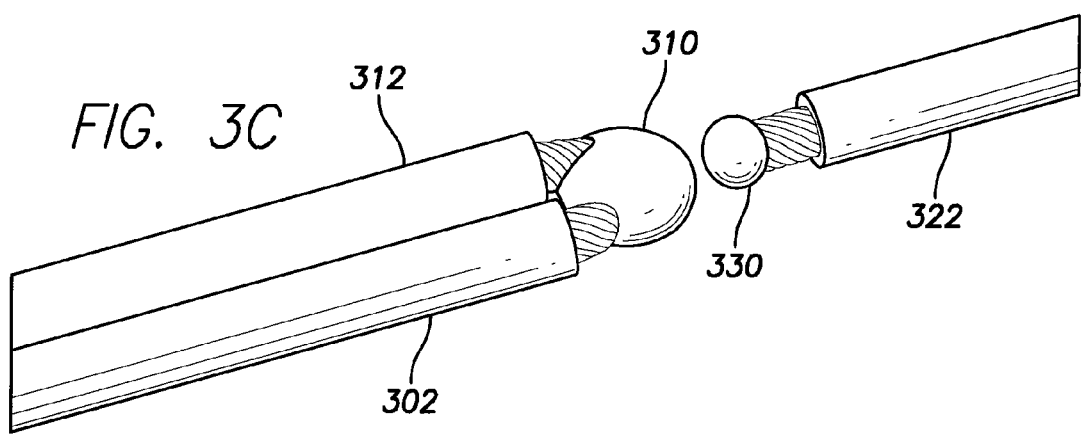
FIG. 3C illustrates a step of an exemplary method for constructing an aligned weld joint according to the embodiment of FIG. 3B.

FIG. 3C illustrates a step of an exemplary method for connecting aligned weld joint 360 described within the embodiment of FIG. 3B. In FIG. 3C, the pair of coated cable conductors 302 and 312 have been electrically and mechanically connected through common nugget 310 using a process described above with respect to FIG. 3A. Further, using the process described with respect to FIG. 2B, laser energy has been applied to an end region of third coated cable conductor 322 to generate a nugget 330. The previously-joined pair of cable conductors 302 and 312 is then aligned opposite of third coated cable conductor 322 such that common nugget 310 is in contact with nugget 330. Laser energy is then applied to thermally fuse common nugget 310 and nugget 330 to form aligned weld joint 360, thereby mechanically and electrically connecting the three coated cable conductors together.

Figure 3D:
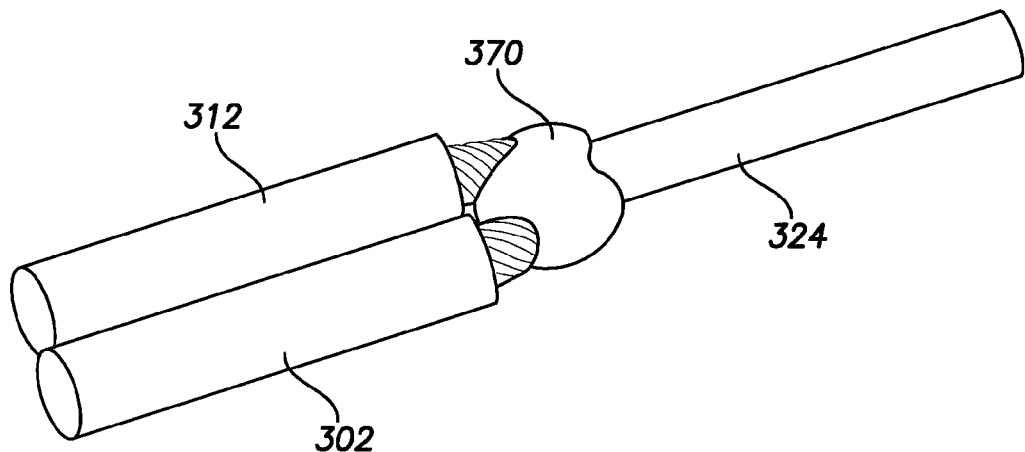
FIG. 3D illustrates an exemplary aligned weld joint that electrically and mechanically connects two coated cable conductors and an uncoated solid wire, in accordance with an embodiment presented herein.

Similarly, an aligned weld joint 370 may be used to join an uncoated solid wire 324 (such as a connector pin) to the pair of coated cable conductors 302 and 312 aligned side-by-side along parallel axes, as shown in FIG. 3D. Aligned weld joint 370 establishes an electrical and mechanical connection between uncoated solid wire 324 and each of coated cable conductors 302 and 312. Further, aligned weld joint 370 requires no additional hardware or material to join uncoated solid wire 324 to the pair of cable conductors 302 and 312 and falls within a dimensional envelope established by cable conductors 302 and 312 and solid wire 324.

Figure 3E:
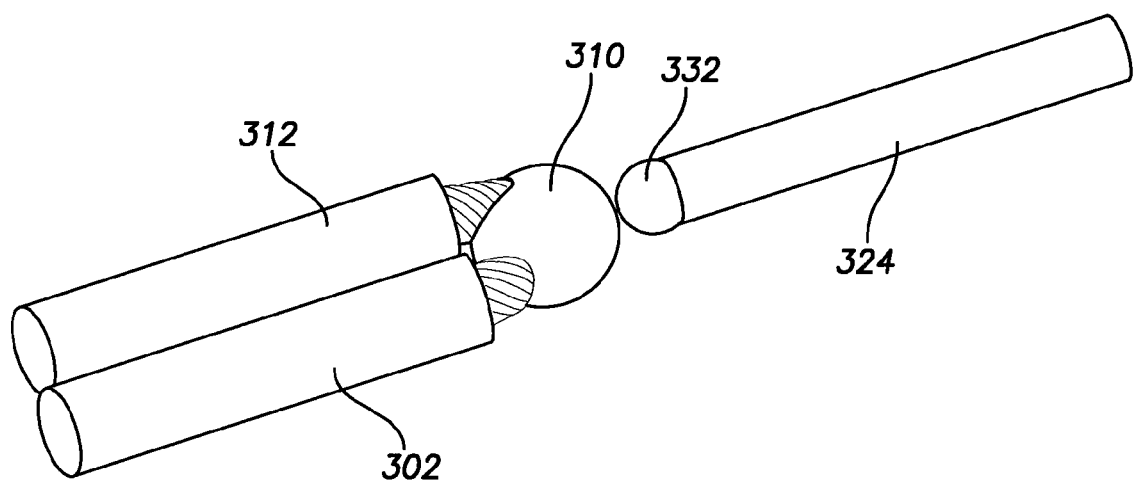
FIG. 3E illustrates a step of an exemplary method for constructing an aligned weld joint according to the embodiment of FIG. 3D.

FIG. 3E illustrates a step of an exemplary method for constructing aligned weld joint 370 shown in FIG. 3D. In FIG. 3E, first coated cable conductor 302 and second coated cable conductor 304 have been aligned in a side-by-side fashion and have been joined together through common nugget 310 using the process described above with respect to FIG. 3A. Further, laser energy has been applied to an end region of uncoated solid wire 324 to melt the wire material and form nugget 332. First and second cable conductors 302 and 322, joined by common nugget 310, are then aligned opposite of solid wire 324 such that common nugget 310 is in contact with nugget 332. Laser energy is then applied to thermally fuse common nugget 310 and nugget 332 to form aligned weld joint 370 shown in FIG. 3D, thereby mechanically and electrically connecting cable conductors 302 and 312 to solid wire 324.

Figure 4A:
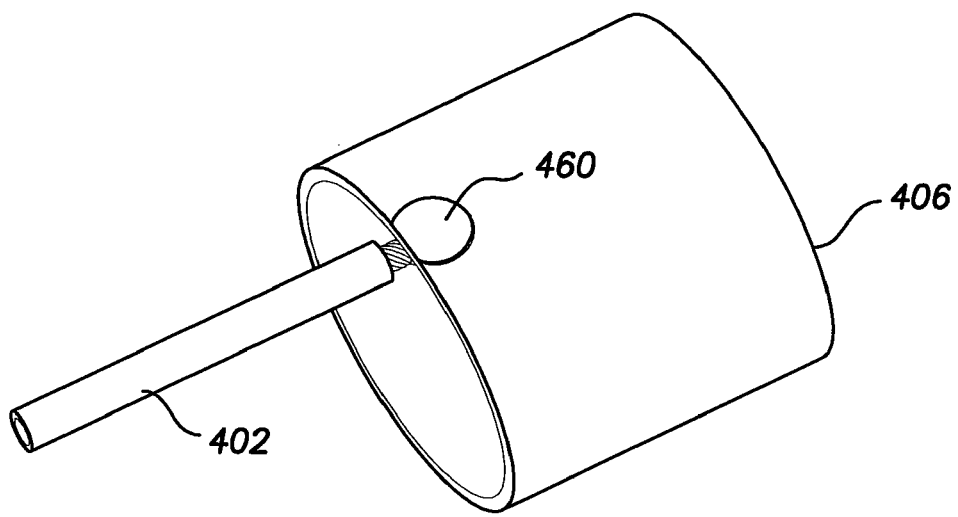
FIG. 4A illustrates an exemplary aligned weld joint that mechanically and electrically connects a cable conductor and an electrode member, in accordance with an embodiment presented herein.

In another embodiment, an aligned weld joint is used to form an electrical and mechanical connection between a conductor, such as a cable conductor or a solid wire, and an electrode member, including but not limited to a ring electrode. FIG. 4A illustrates an exemplary aligned weld joint 460 that forms an electrical and mechanical connection between a coated cable conductor 402 and a ring electrode 406. In contrast to the conventional joint shown in FIGS. 1A and 1B, aligned weld joint 460 requires neither additional hardware, such as crimp sleeve 104, nor additional material, such as solder or flux, to join coated cable conductor 402 to electrode 406. In further contrast to the conventional joint shown in FIG. 1B, aligned weld joint 460 neither increases the outer diameter $D_{OUT}$ of the ring electrode nor decreases the inner diameter $D_{IN}$ of the ring electrode, as shown in the cross-sectional view of FIG. 4B.

Figure 4B:
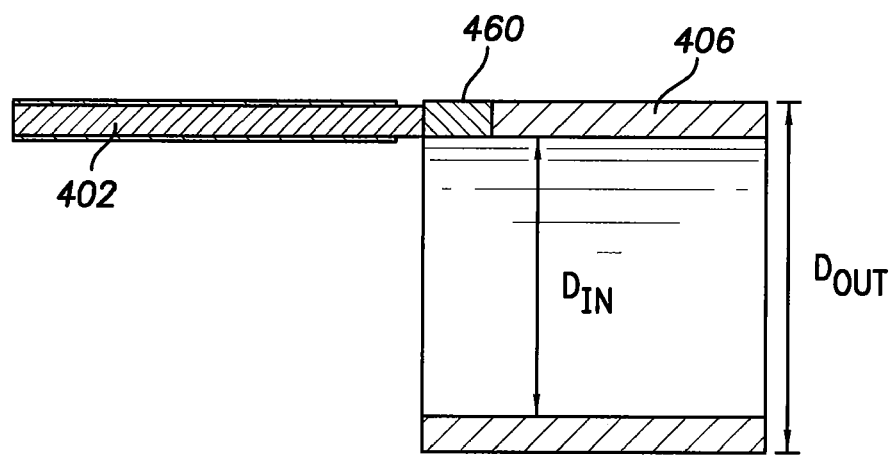
FIG. 4B is a cross-sectional view of the exemplary aligned weld joint shown in FIG. 4A.
Figure 4C:
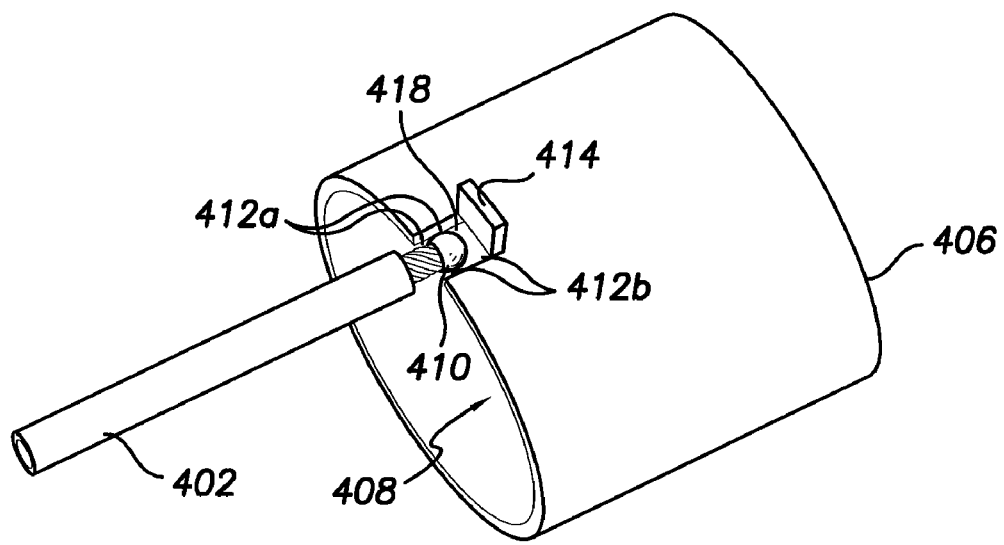
FIG. 4C illustrates an exemplary method for constructing an aligned weld joint according to the embodiment of FIGS. 4A and 4B.

FIG. 4C describes an exemplary method for constructing aligned weld joint 460 according to the embodiment of FIGS. 4A and 4B. Using the process described with reference to FIG. 2B, laser energy has been applied to coated cable conductor 402 to ablate the coating material and melt the underlying cable into a nugget 410. Further, laser energy has been applied to ring electrode 406 to ablate electrode material and allow a portion of a peripheral edge 408 of electrode 406 to be peeled away from an outer surface of electrode 406, thus forming tab 414 and exposing a groove 418 in electrode 406. In the embodiment of FIG. 4C, tab 414 extends away from electrode 406 such that tab 414 is positioned perpendicular to the outer surface of electrode 406.

In one embodiment, tab 414 may be formed by cutting (by applying laser energy or sawing, for example) passages 412a and 412b through the outer surface of electrode 406. Passages 412a and 412b extend away from peripheral edge 408 in an axial direction for a specified distance, and tab 414 is folded away from peripheral end 408 and passages 412a and 412b. In the embodiment of FIG. 4C, the specified distance is a multiple of a diameter of nugget 410, although in additional embodiments, passages 412a and 412b may extend from peripheral edge 408 for a distance equivalent to one-half of the diameter of nugget 410.

Coated cable 402 is aligned with electrode 406 such that nugget 410 is positioned within groove 418, as shown in FIG. 4C. In alternate embodiments, nugget 410 may be placed in contact with tab 414. Laser energy is delivered to tab 414 and nugget 410, and the delivered energy melts tab 414 and nugget 410 together, with tab 414 providing filler material to weld coated cable conductor 402 in groove 418. Resulting aligned weld joint 460 mechanically and electrically connects coated cable conductor 402 to electrode 406, requires no additional hardware or material, and increases neither an inner diameter nor an outer diameter of the electrode.

Figure 4D:
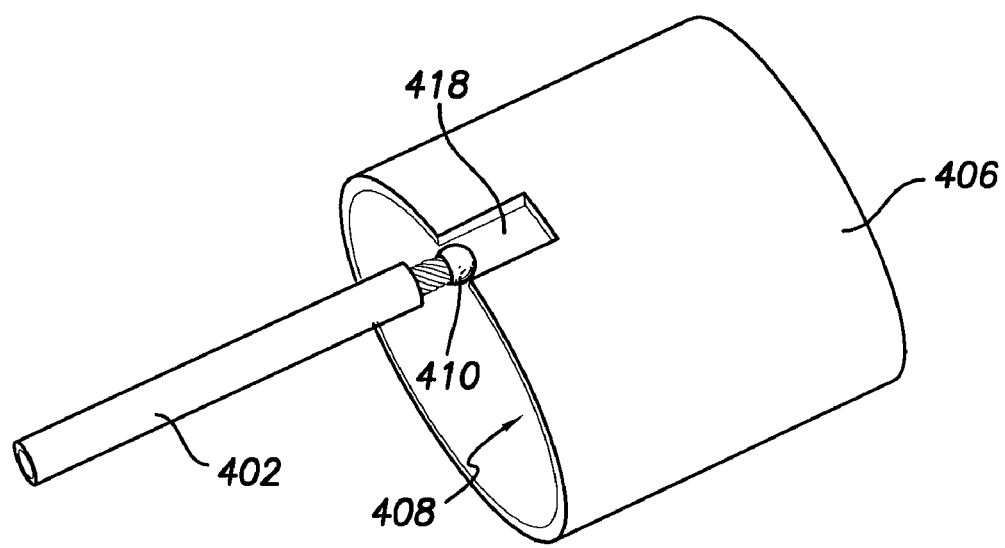
FIG. 4D illustrates another exemplary method for constructing an aligned weld joint according to the embodiment of FIGS. 4A and 4B.

FIG. 4D describes a second exemplary method for constructing aligned weld joint 460 according to the embodiments of FIGS. 4A and 4B. As described above, laser energy has been delivered to an end of cable conductor 402 to form nugget 410. Laser energy is then delivered to electrode 406 to ablate electrode material and form groove 418 in electrode 406. Alternatively, the laser energy may be delivered to electrode 406 to cut passages along a perimeter of groove 418 to free material from the surface of electrode 406, which may then be removed to yield groove 418. Coated cable conductor 402 is then aligned with electrode 406 such that nugget 410 is positioned within groove 418. Laser energy is delivered to nugget 410 to melt nugget 410 to fill in groove 418 and fuse coated cable conductor 402 into groove 418, thereby forming aligned weld joint 460. Aligned weld joint 460 mechanically and electrically connects coated cable conductor 402 to electrode 406, while requiring no additional hardware or material and increasing neither the inner diameter nor the outer diameter of electrode 406.

The embodiments of FIGS. 4A-4D describe aligned weld joints that join together a coated cable conductor and an electrode member. In alternate embodiments, two (or more) coated cable conductors may be joined together through a common nugget using the process outlined above in FIG. 3A. Using the processes described in FIGS. 4C and 4D, these coated conductors may be electrically and mechanically connected to electrode 406 through aligned weld joint 460. Further, although described in terms of coated cable conductors, the methods of FIGS. 4C and 4D may connect a variety of conducting elements to electrode 406 through aligned weld joint 460, including but not limited to uncoated cable conductors, coated solid wires, and uncoated solid wires.

Figure 5A:
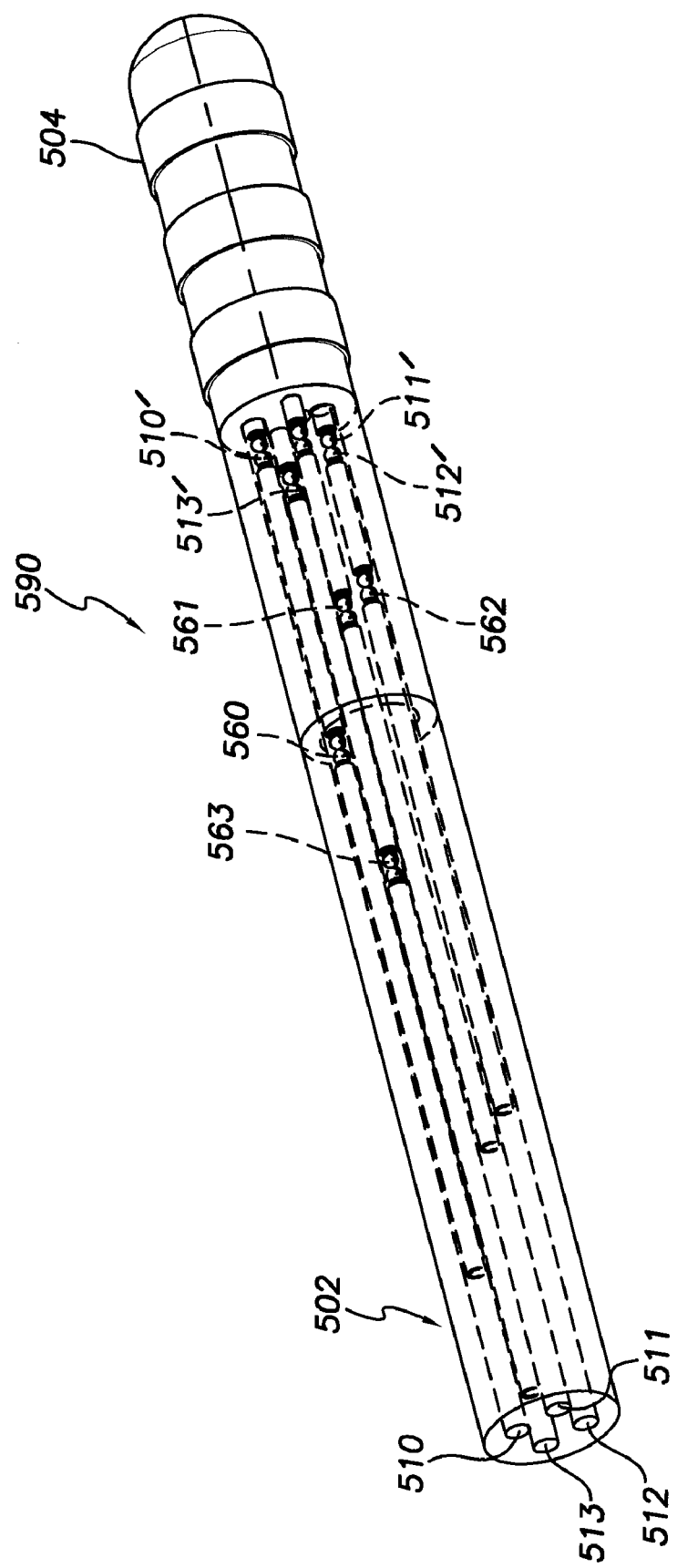
FIG. 5A is illustrates an exemplary portion of modular, body-implantable lead incorporating aligned weld joints, in accordance with an embodiment presented herein.

FIG. 5A illustrates an exemplary portion of a body-implantable lead 590 that may be modularly constructed from an exemplary lead body, shown generally at 502, and an exemplary distal tip, shown generally at 504. Lead body 502 contains four inner lumens respectively housing coated cable conductors 510, 511, 512, and 513. Further, four coated cable conductors 510', 511', 512', and 513' extend from a proximal end of distal tip 504. Coated cable conductors 510, 511, 512, and 513 from lead body 502 have been connected to corresponding coated cable conductors 510', 511', 512', and 513' from distal tip 504 through a series of aligned weld joints 560, 561, 562, and 563 so as to form conduction paths there between. As described above, the aligned weld joints fall within an existing dimensional envelope of each coaxially-joined pair of coated cable conductors, and the cumulative effect of the joints does not extend beyond a dimensional envelope of the lead body. As such, an outer diameter of body-implantable lead 590 depends only on a maximum outer diameter established by lead body 502 and distal tip 504.

Figure 5B:
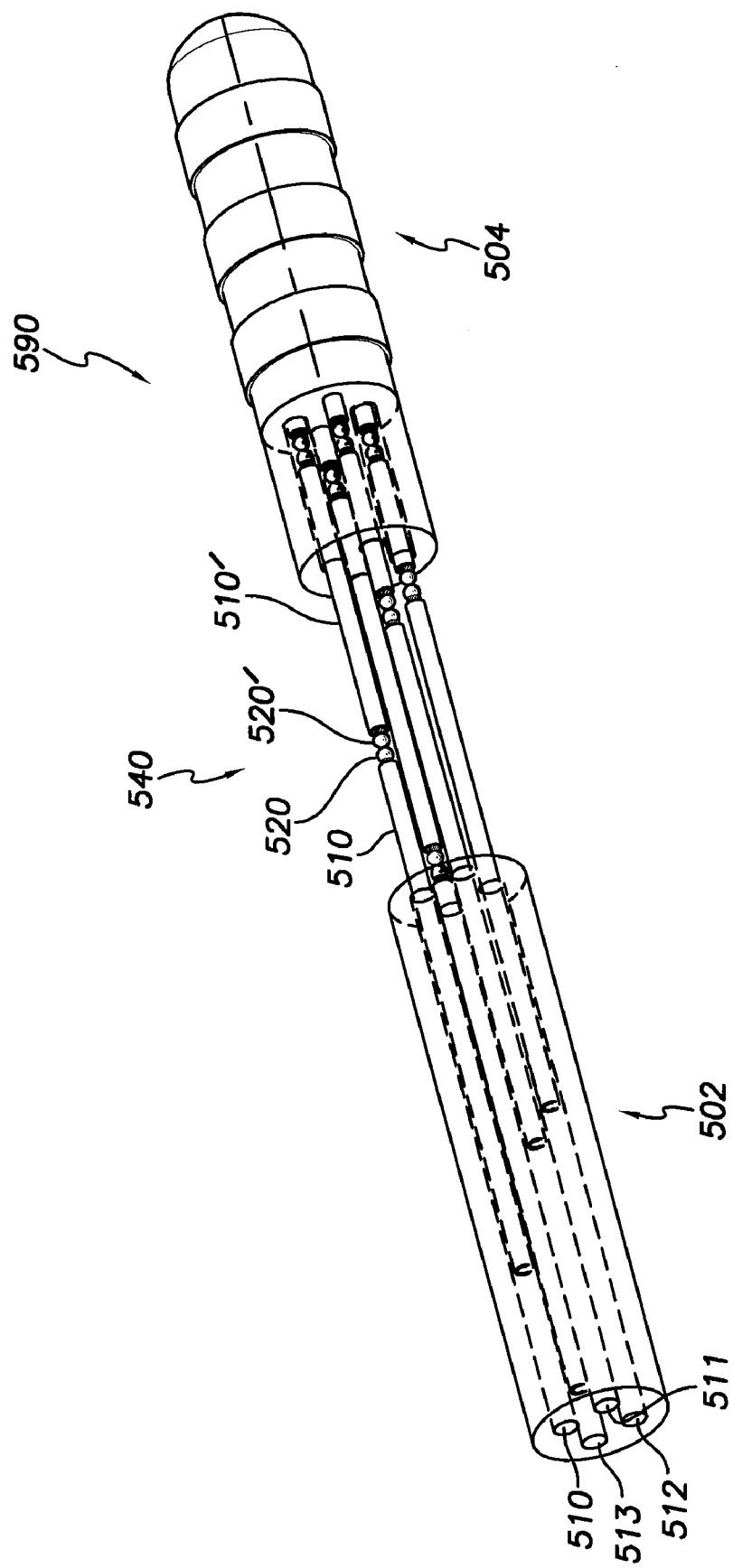
FIGS. 5B and 5C illustrate steps of an exemplary method for constructing a modular, body-implantable lead according to the embodiment of FIG. 5A.
Figure 5C:
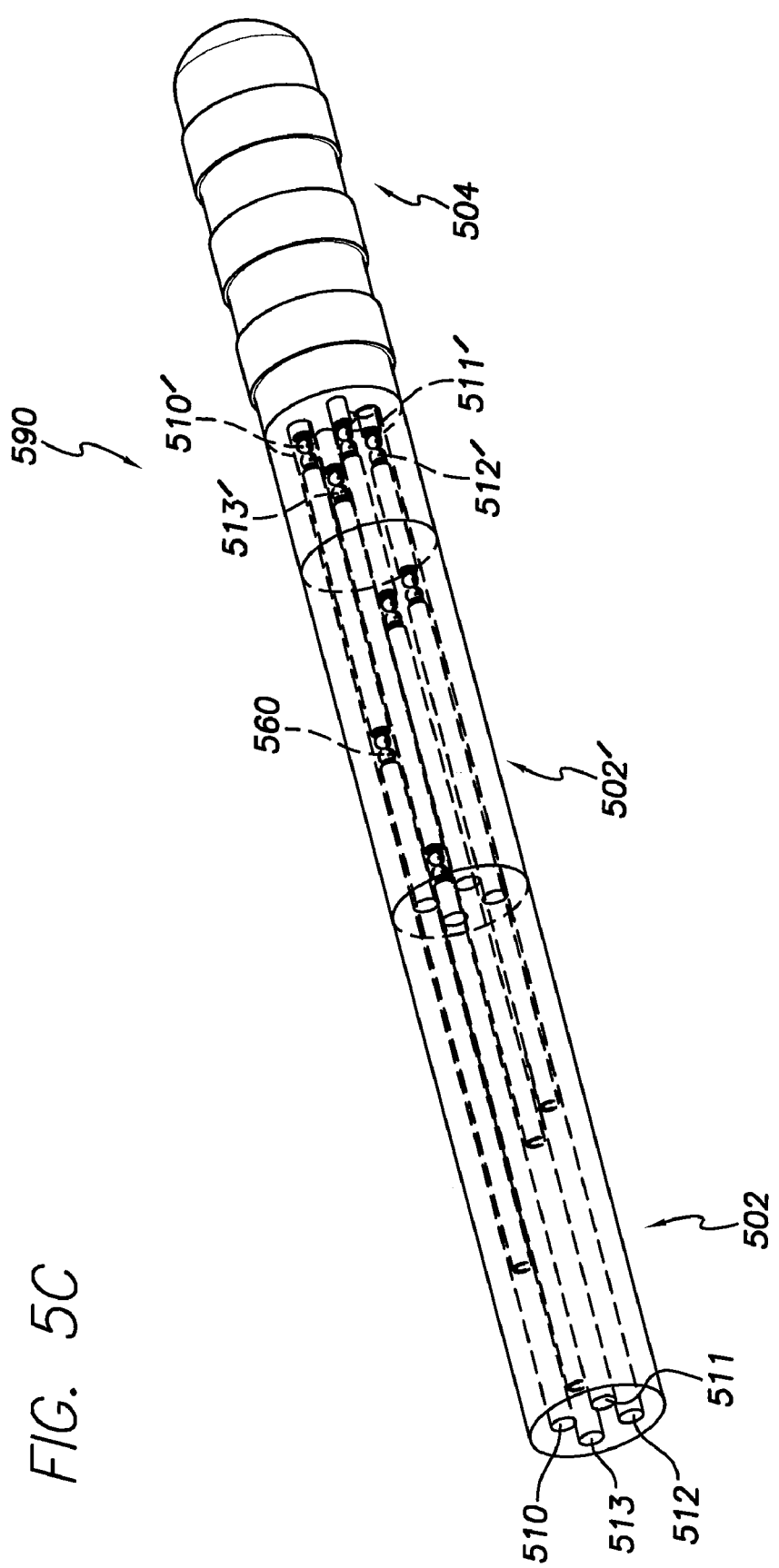

FIGS. 5B and 5C illustrate steps of an exemplary method for constructing body-implantable lead 590 shown in FIG. 5A. In FIG. 5B, laser energy has been applied to a distal end of each cable conductor 510, 511, 512, and 513 extending from the inner lumens of lead body 502. As described above with reference to FIG. 2B, the applied laser energy ablates the coating material from each respective conductor and melts the underlying cable to form nuggets on coated cable conductors 510, 511, 512, and 513. For example, laser energy applied to cable conductor 520 ablates the coating material and melts the underlying cable to form nugget 520. In a similar fashion, laser energy has been applied to a proximal end of cable conductors 510', 511', 512', and 513' to ablate the coating material and melt the underlying cable to form nuggets on cable conductors 510', 511', 512', and 513'. For example, the applied laser energy has ablated the coating material and melted the underlying cable of coated cable conductor 510' to form nugget 520'.

Lead body 502 and distal tip 522 are then positioned such that coated cable conductors 510, 511, 512, and 513 of lead body 502 are coaxially aligned with corresponding coated cable conductors 510', 511', 512', and 523' that protrude from distal tip 504. Further, nuggets on coated cable conductors 510, 511, 512, and 513 are respectively placed into contact with corresponding nuggets on coated cable conductors 510', 511', 512', and 513' within a transition zone 540. For example, conducting cable 510, which is housed within lead body 502, may be coaxially aligned with conducting cable 510' such that nugget 520 of coated cable conductor 510 is in contact with nugget 520' of coated cable conductor 510' within transition zone 540.

In FIG. 5C, laser energy has been applied to each pair of nuggets within transition zone 540 to fuse the nuggets into aligned weld joints that mechanically and electrically connect each respective pair of coated cable conductors. For example, laser energy is applied to fuse nuggets 520 and 520' to form aligned weld joint 560 that joins together cable conductors 510 and 510', thus forming an electrical path between lead body 502 and distal tip 504 along joined coated cable conductors 510 and 510'.

In another embodiment (not shown), two coated cable conductors, such as cable conductors 510 and 511 housed in lead body 502, may be joined together by common nugget 310 described above with reference to FIG. 3A. These joined cables 510 and 511 may then be aligned with cable conductor 510' from the distal tip such that common nugget 310 is in contact with nugget 510'. Using the process outlined in FIGS. 3B-3C, laser energy may be applied to fuse nuggets 310 and 510' to form an aligned weld joint, such as aligned weld joint 360, that mechanically and electrically connects conductors 510 and 511 to conductor 510', thus forming distinct conduction paths from the distal tip to the lead body along joined conductor pairs 510' and 510 and 510' and 511.

Once aligned weld joints have been formed to connect each pair of cable conductors within body-implantable lead 590, an electrically-insulating and biologically-inert material, such as liquid silicone rubber (LSR), is molded about the aligned weld joints within transition zone 540 to form lead body portion 502' at transition zone 540. The molding process efficiently utilizes space and fills gaps that may exist between the cable conductors and between the conductors and the lead body. Further, the use of an electrically insulating-material such as LSR may insulate each aligned weld joint from its surrounding joints. The aligned weld joints fall within the existing dimensional envelope of each pair of coated cables, and the cumulative effect of the joints does not extend beyond the dimensional envelope of the lead body. Further, lead body portion 502' at transition zone 540 is iso-diametric with lead body 502, and lead body portion 502' may have a diameter that does not vary along transition zone 540.

Figure 6A:
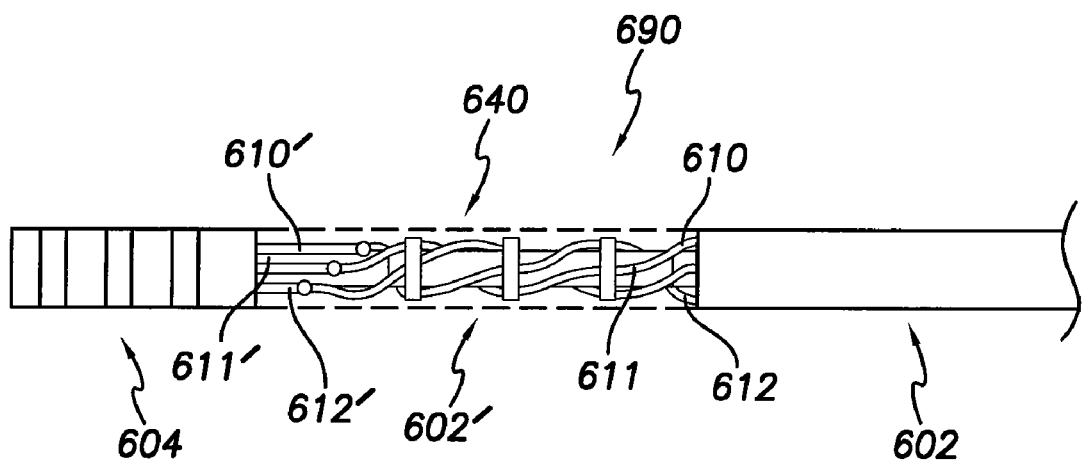
FIG. 6A illustrates a second exemplary portion of a modular, body-implantable lead incorporating aligned weld joints, in accordance with an embodiment presented herein.

FIG. 6A illustrates an exemplary portion of a body-implantable lead 690 that may be modularly constructed from an exemplary lead body, shown generally at 602, and an exemplary proximal connector, shown generally at 604. In this embodiment, lead body 602 has three inner lumens, each of which houses one of coated cable conductors 610, 611, and 612. Further, three elongated, uncoated solid wire connector pins 610', 611', and 612' protrude from a distal end of proximal connector 604 at staggered lengths, and an aligned weld joint connects each connector pin to a corresponding coated cable conductor from lead body 602 within a transition zone 640. In the embodiment of FIG. 6A, the coated cable conductors are then positioned in a helical configuration within the transition zone, and an electrically-insulating and biologically-inert material is molded around the joined cable conductors and connector pins within the transition zone to form lead body portion 602' (shown in phantom lines).

As described above, the individual aligned weld joints fall within the respective existing dimensional envelope of the coated cable conductor and the solid wire connector pin, and the cumulative effect of the joints does not extend beyond the dimensional envelope of lead body 602 (including lead body portion 602'). As such, an outer diameter of body-implantable lead 690 depends only on a maximum outer diameter established by lead body 602 and proximal connector 604 independent of the existence of conductor joints.

Figure 6B:
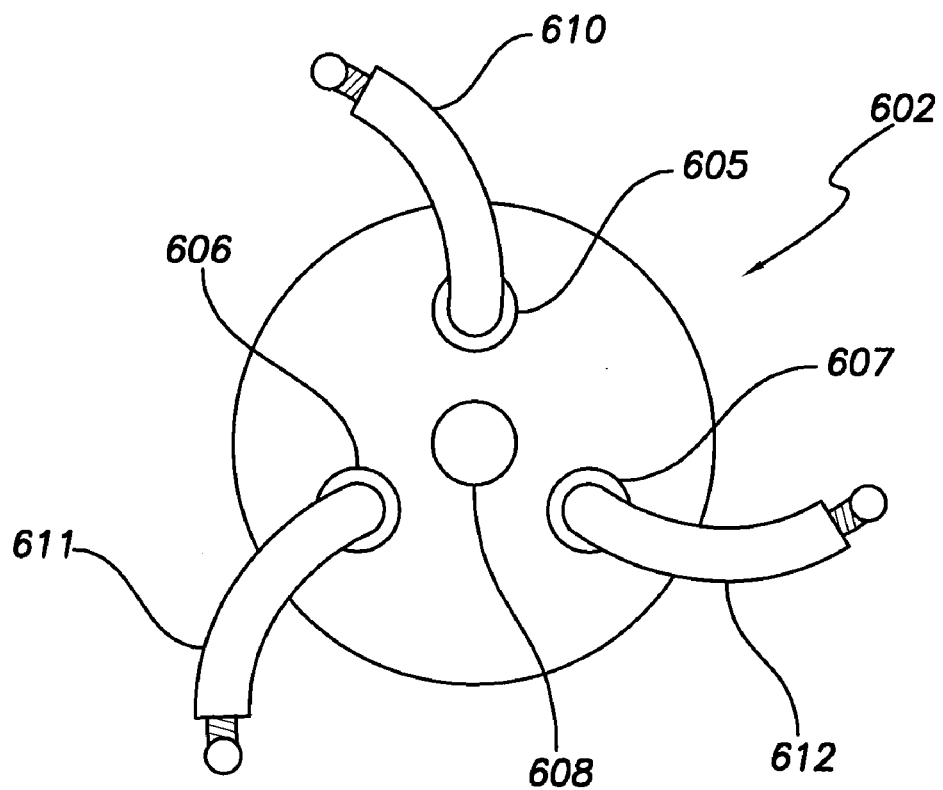
FIGS. 6B and 6C are cross-sectional views of a lead body and a proximal connector, respectively, that may be incorporated into the modular, body-implantable lead of FIG. 6A.

FIG. 6B is a cross-sectional view of exemplary lead body 602 of lead 690. In FIG. 6B, lead body 602 incorporates three inner lumens shown at 605, 606, and 607. Each inner lumen 605, 606, and 607 within lead body 602 respectively houses cable conductors 610, 611, and 612. Further, lead body 602 may additionally incorporate a central lumen 608 for receiving a stylet or a guidewire to provide control of or rigidity to the lead during implantation.

Figure 6C:
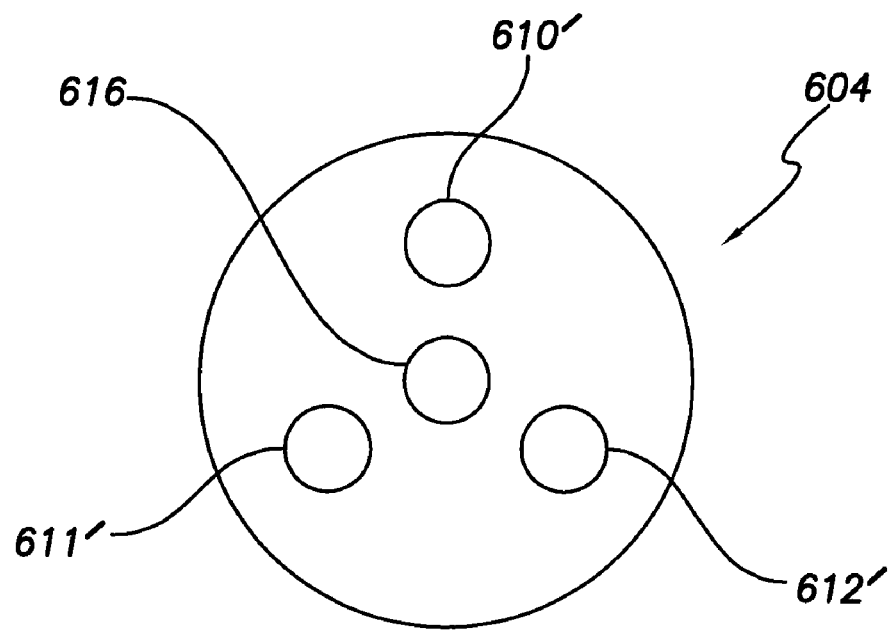

FIG. 6C is a cross-sectional view of exemplary proximal connector 604 of lead 690. In FIG. 6C, three uncoated, solid wire connector pins 610', 611', and 612' protrude from proximal connector 604. Connector pins 610', 611', and 612' may protrude from proximal connector 604 at staggered lengths, or in alternate embodiments, connector pins 610', 611', and 612' may be of uniform length. Connector 604 may also include a central lumen 616 for receiving a stylet or a guidewire.

Figure 6D:
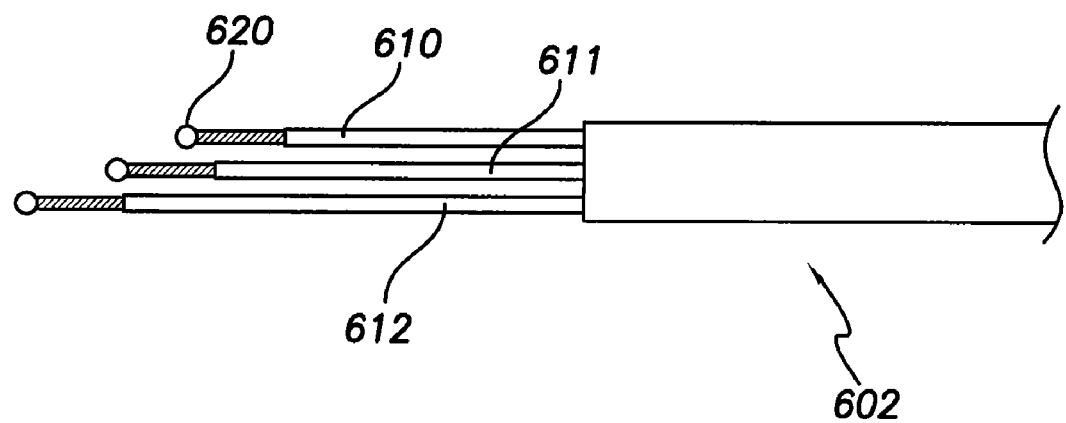

FIGS. 6D, 6E, and 6F illustrate steps of an exemplary method for constructing body-implantable lead 690. In FIG. 6D, laser energy has been applied to coated cable conductors 610, 611, and 612 to cut the cable conductor to a specified length, to ablate coating material, and to melt the underlying cable material to form a nugget, such as nugget 620 on cable conductor 610. The applied laser energy cuts cable conductors 610, 611, and 612 to staggered lengths, and in the embodiment of FIG. 6D, cable conductor 610 is shorter in length than cable conductors 611 and 612. In alternate embodiments, the applied laser energy may cut cable conductors 610, 611, and 612 to any combination of staggered lengths that would be apparent to one skilled in the art. Although not shown in FIG. 6D, a similar process may be applied to connector pins 610', 611', and 612' to cut the connector pins to a specified length, ablate any coating material, and melt the underlying pin material to form a nugget on each connector pin, such as nugget 620' on connector pin 610' in FIG. 6E.

In FIG. 6E, lead body 602 and proximal connector 604 are positioned such that coated cable conductors 610, 611, and 612 of lead body 602 are coaxially aligned with corresponding connector pins 610', 611', and 612' of proximal connector 602. Further, nuggets disposed on cable conductors 610, 611, and 612 are placed into contact with corresponding nuggets on connector pins 610', 611', and 612' within transition zone 640. For example, coated cable conductor 610 is coaxially aligned with connector pin 610' such that nugget 620 is in contact with nugget 620' within transition zone 640.

In FIG. 6F, laser energy is applied to each pair of nuggets within transition zone 640, and the applied energy fuses the nuggets into aligned weld joints that mechanically and electrically connect cable conductors 610, 611, and 612 to corresponding conductors 610', 611', and 612'. For example, laser energy has been applied to fuse nuggets 620 and 620' and form an aligned weld joint 660 that connects coated cable conductor 610 to connector pin 610', thus forming an electrical path between lead body 602 and proximal connector 604 along joined conductors 610 and 610'.

In additional embodiments (not shown), two coated cable conductors, such as cable conductors 610 and 611 housed in lead body 602, may be joined together through a common nugget using the procedures described above with reference to FIG. 3A. Cables 610 and 611 may then be aligned with connector pin 610' such that the common nugget is in contact with nugget 620'. Using the processes outlined in FIGS. 6D-6F, laser energy may be applied to fuse these nuggets together to form an aligned weld joint that mechanically and electrically connects coated cable conductors 610 and 611 to solid wire connector pin 610', thus forming distinct electrical paths between proximal connector 604 and lead body 602 along joined conductors 610' and 610 and 610' and 611.

In FIG. 6F, once the aligned weld joints have been formed, the coated cable conductors are then positioned in a helically-twisted configuration within transition zone 640. Such a configuration reduces stresses within the cable conductors of the body-implantable lead and improves the flexibility of lead 690. In the embodiment of FIG. 6F, a series of support disks 680, 681, and 682 are disposed within transition zone 640 to aid in positioning the coated cable conductors in the helically-twisted configuration. Support disks 680, 681, and 682 may be constructed such that coated cable conductors 610, 611, and 612 individually snap into appropriate positions within support disks 680, 681, and 682.

Once coated cable conductors 610, 611, and 612 have been positioned in the helically-twisted configuration, a biologically-inert and electrically-insulating material, such as liquid silicone rubber (LSR), may be molded about the aligned weld joints within transition zone 640 to form lead body portion 602' illustrated in FIG. 6A. The molding process efficiently utilizes space and fills air gaps that may exist between the cable and pin conductors and between the conductors and the lead body. The use of an electrically insulating material such as LSR may also insulate each aligned weld joint from its surrounding joints. The aligned weld joints fall within the existing dimensional envelope of each pair of connector pin and cable conductor, and the cumulative effect of the joints does not extend beyond the dimensional envelope of the lead body. Further, lead body portion 602' at transition zone 640 is iso-diametric with lead body 602 and may have a diameter that does not vary along transition zone 640.

Figure 7:
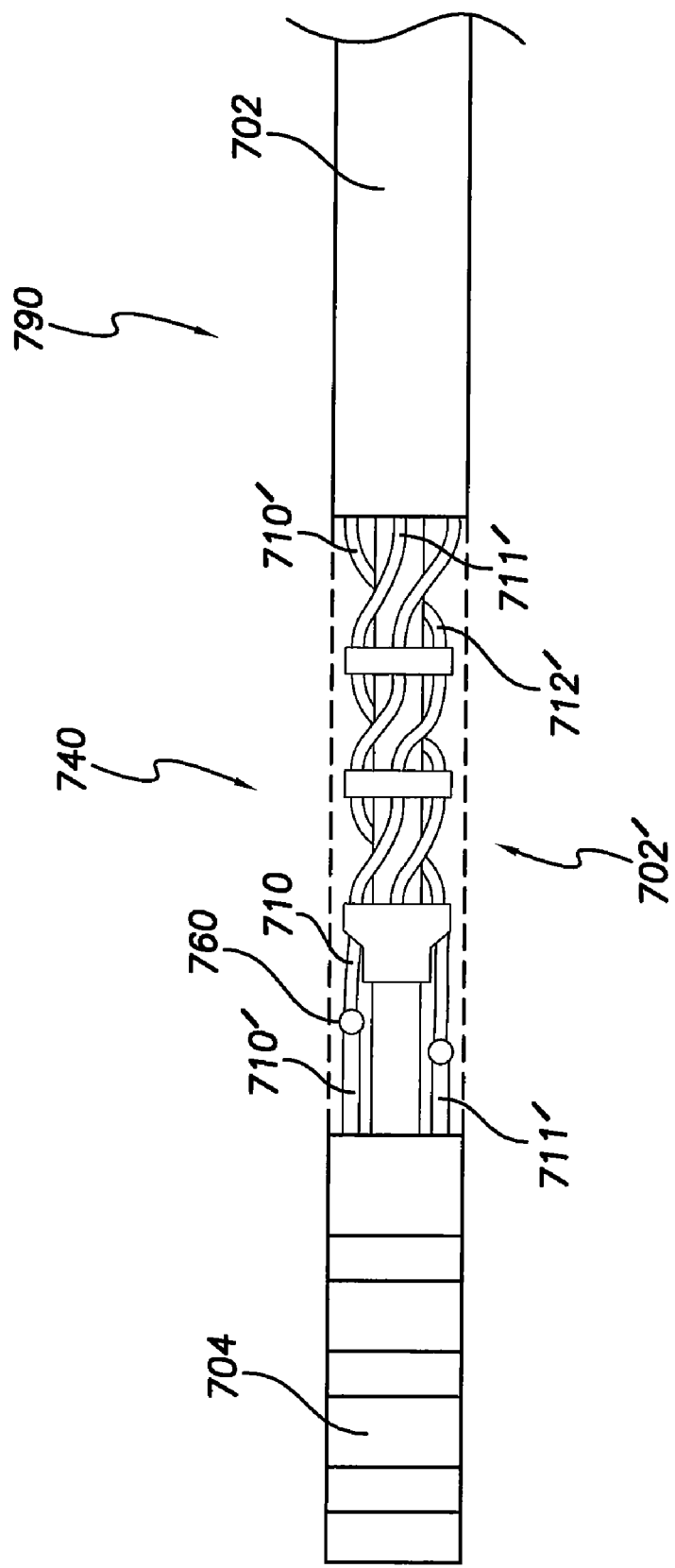
FIG. 7 illustrates a third exemplary portion of a modular, body-implantable lead incorporating aligned weld joints, in accordance with an embodiment presented herein.

FIG. 7 illustrates an exemplary portion of a body-implantable lead 790 that may be modularly constructed from an exemplary lead body, shown generally at 702, and an exemplary proximal connector, shown generally at 704, in accordance with another embodiment presented herein. Lead body 702 comprises three inner lumens, each of which houses one of coated cable conductors 710, 711, and 712, and the inner lumens and coated cable conductors within lead body 702 are disposed about a central lumen (not shown). Further, three elongated, uncoated solid wire connector pins 710', 711', and 712' (not shown) protrude from proximal connector 704, and in contrast to the embodiment of FIG. 6A, the uncoated, solid wire connector pins are of equivalent length and are not staggered and are disposed about a central lumen 716. The connector pins protruding from proximal connector 704 are respectively connected to corresponding cable conductors protruding from lead body 702 within a transition zone 740 through aligned weld joints 760. Further, an electrically insulating and biologically inert material may be molded around the joined cable conductors and connector pins within transition zone 740 to form body-implantable lead body portion 702' (shown in phantom lines).

Each aligned weld joint falls within the existing dimensional envelope of the coated cable conductor and the solid wire connector pin, and the cumulative effect of the joints does not extend beyond the dimensional envelope of lead body 702, and lead body portion 702' can be iso-diametric with lead body 702. As such, an outer diameter of lead 790 depends only on a maximum outer diameter established by lead body 702 and proximal connector 704.

In the embodiments described above, the coated cable conductors are housed within inner lumens, which themselves may be pre-formed within the lead body. However, in alternate embodiments, a lead body may be formed by molding a biologically-inert and electrically-insulating material about a number of coated cable conductors disposed in a helically-twisted configuration, as in FIGS. 6A-6F and 7, or disposed side-by-side along parallel axes, as in FIGS. 5A-5C. In one such embodiment, a liquid injection molding (LIM) process may be used to mold liquid silicone rubber (LSR) material about the coated cable conductors to create the lead body. The resultant lead body may or may not include an additional insulating outer coating or employ the reinforcing techniques that are common in conventional lead bodies. The resultant lead body efficiently uses space, as no air gaps exist between the conductor cables and/or pins and between these conductors and the lead body.

Further, the lead bodies formed using the liquid injection molding process support the modular body-implantable lead design described above with respect to FIGS. 5A-5C, 6A-6F, and 7. The conductors within modular molded lead bodies may be joined to modular proximal connectors, distal tips, and additional lead bodies using aligned weld joints, thereby permitting easy assembly of leads having a variety of different lengths, proximal connectors, and distal tips. Additional biologically-inert and electrically-insulating materials may then be molded about the aligned weld joints located at a transition zone, resulting in a joint area iso-diametric with the lead body and the proximal and distal ends. Liquid injection molding using liquid silicone rubber or other materials, or any other suitable molding technique and insulating material, may be used to construct the lead body as should be apparent to one skilled in the art.

The foregoing embodiments describe aligned weld joints that join together coated cable conductors with each other or with uncoated solid wires and electrode rings. The aligned weld joints described herein are not limited to such conducting elements. Coated or uncoated cable conductors may be joined to coated or uncoated wires using aligned weld joints. Further, uncoated cable conductors may be joined together; coated or uncoated solid wires may be joined together; and cables and wires may be joined together or to an electrode. In additional embodiments, any number of conducting elements, such as coated or uncoated cable conductors, coated or uncoated solid wires, and any number of additional conducting elements may be joined together by a common nugget, which may in turn be joined to any number of other conducting elements having a common nugget via an aligned weld joint similar to the embodiments described above with reference to FIGS. 3A-3E. Further, the embodiments described herein are not limited to conducting elements composed of a specific underlying material or coated with a specific material. One skilled in the art should recognize that the aligned weld joints described herein may be used to connect conducting elements of various compositions that may be coated with various materials.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A body-implantable lead, comprising:
   a lead body having at least one inner lumen;
   at least one elongated conductor cable residing within the inner lumen, wherein an end portion of the conductor cable is joined by an aligned weld joint directly to an end portion of a lead component; and further comprising
   a second elongated conductor cable residing within a second inner lumen of the lead body and extending side-by-side and parallel to the at least one elongated conductor cable, wherein an end portion of the second conductor cable is joined to the end portion of the at least one elongated conductor cable, and wherein the joined ends of the conductor cables are joined by an aligned weld joint directly to the end portion of the lead component.

2. The body-implantable lead of claim 1, wherein the lead component is an elongated conductive connector pin of a proximal connector, the end portion of the conductor cable being joined by an aligned weld joint directly to the end portion of the connector pin.

3. The body-implantable lead of claim 2, wherein the connector pin is a wire.

4. The body-implantable lead of claim 2, wherein a second end portion opposite of the first end portion of the conductor cable is joined by an aligned weld joint directly to a ring electrode.

5. The body-implantable lead of claim 1, wherein the lead component is a conductor extending from a proximal end of a distal tip of the lead, the end portion of the conductor cable being joined by an aligned weld joint directly to the end portion of the distal tip conductor.

6. The body-implantable lead of claim 5, wherein a second end portion opposite of a first end portion of the conductor cable is joined by an aligned weld joint directly to an end portion of an elongated conductive connector pin of a proximal connector.

7. The body-implantable lead of claim 6, wherein at least one of the proximal connector and the distal tip conductor are modular.

8. A body-implantable lead, comprising:
   a lead body having at least one inner lumen;
   at least one elongated conductor cable residing within the inner lumen, wherein an end portion of the conductor cable is joined by an aligned weld joint directly to an end portion of a lead component;
   wherein the lead component is an electrode member, the end portion of the conductor cable being joined by an aligned weld joint directly to the end portion of the electrode member;
   wherein a second end portion opposite of a first end portion of the conductor cable is joined by an aligned weld joint directly to an end portion of a second lead component; and
   wherein the second lead component is a second conductor cable.

9. A method for assembling a body-implantable lead, comprising:
   providing a lead body having at least one inner lumen with at least one elongated conductor cable extending within the inner lumen; and
   joining an end portion of the conductor cable directly to an end portion of a lead component using an aligned weld joint;
   wherein the lead component is an electrode member, the end portion of the conductor cable being joined by an aligned weld joint directly to the end portion of the electrode member;
   wherein the joining step comprises forming a groove in the electrode member and securing the end portion of the conductor cable within the groove with the aligned weld joint; and
   wherein the electrode member is a ring electrode, and wherein the forming step comprises one of (i) delivering energy to ablate material from a peripheral end of the electrode and (ii) bending a portion of a peripheral end of the electrode away from a surface of the electrode so as to form a tab adjacent the groove.

10. The method of claim 9, wherein the providing the lead body step includes forming the lead body by molding liquid insulation material about the conductor cable so as to substantially eliminate air gaps between the conductor cable and the lead body.

11. The method of claim 9, further comprising molding insulating material about the aligned weld joint so that the body-implantable lead is iso-diametric.

12. A method for assembling a body-implantable lead, comprising:
   providing a lead body having at least one inner lumen with at least one elongated conductor cable extending within the inner lumen;
   joining an end portion of the conductor cable directly to an end portion of a lead component using an aligned weld joint;
   wherein the lead component is an electrode member, the end portion of the conductor cable being joined by an aligned weld joint directly to the end portion of the electrode member;
   wherein the joining step comprises forming a groove in the electrode member and securing the end portion of the conductor cable within the groove with the aligned weld joint; and
   wherein the forming step comprises bending a portion of a peripheral end of the electrode away from a surface of the electrode so as to form a tab adjacent the groove, and wherein the securing step includes melting the tab so that the melted tab provides filler material around the cable in the groove.

* * * * *